(12) United States Patent
Lee et al.

(10) Patent No.: US 11,058,968 B2
(45) Date of Patent: **\*Jul. 13, 2021**

(54) SALT REMOVAL AND TRANSPORT SYSTEM AND METHOD FOR USE IN A MONO ETHYLENE GLYCOL RECLAMATION PROCESS

(71) Applicant: Cameron Solutions, Inc., Houston, TX (US)

(72) Inventors: Joseph Min-Hsiun Lee, Houston, TX (US); Gary W. Sams, Spring, TX (US)

(73) Assignee: CAMERON SOLUTIONS, INC., Houston, TX (US)

( \* ) Notice: Subject to any disclaimer, the term of this patent is extended or adjusted under 35 U.S.C. 154(b) by 0 days.

This patent is subject to a terminal disclaimer.

(21) Appl. No.: 16/366,130

(22) Filed: Mar. 27, 2019

(65) Prior Publication Data

US 2019/0217219 A1    Jul. 18, 2019

Related U.S. Application Data

(60) Division of application No. 15/494,985, filed on Apr. 24, 2017, now Pat. No. 10,252,182, which is a
(Continued)

(51) Int. Cl.
  *B01D 1/30*    (2006.01)
  *C07C 29/80*    (2006.01)
(Continued)

(52) U.S. Cl.
  CPC .............. *B01D 1/30* (2013.01); *B01D 3/065* (2013.01); *C07C 29/76* (2013.01); *C07C 29/80* (2013.01)

(58) Field of Classification Search
  CPC ............ B01D 1/30; B01D 3/065; C07C 29/76
  See application file for complete search history.

(56) References Cited

U.S. PATENT DOCUMENTS

| 2001/0018897 | A1 | 9/2001 | Schmidt et al. |
| 2007/0160513 | A1 | 7/2007 | Steil et al. |
| 2013/0118989 | A1 | 5/2013 | Fernandez et al. |

FOREIGN PATENT DOCUMENTS

| EP | 0090335 A2 | 10/1983 |
| EP | 0436973 A2 | 7/1991 |

(Continued)

OTHER PUBLICATIONS

Cameron: "Puremeg-Meg Reclamation and Regeneration Technology", Jan. 1, 2013.
(Continued)

*Primary Examiner* — Lessanework Seifu
(74) *Attorney, Agent, or Firm* — Helene Raybaud

(57) ABSTRACT

Systems and methods for removing solids from a process stream being fed into a flash separator include a solids fluidization device and a solids removal device. The solids fluidization device at the bottom end of the fluid column of the flash separator introduces a swirling motive fluid within the fluid column, while the solids removal device located above the solids fluidization device removes the slurry created by the swirling motive fluid. Systems and methods for fluidizing solids in the fluid column of a flash separator include a solids fluidization device that introduces a swirling motive fluid within the fluid column, means to limit the upward movement of the swirling motive fluid, such as a valve, and removing the solid slurry produced by the swirling motive fluid.

20 Claims, 3 Drawing Sheets

Related U.S. Application Data continuation of application No. 15/056,256, filed on Feb. 29, 2016, now Pat. No. 9,630,122, which is a continuation of application No. 14/307,232, filed on Jun. 17, 2014, now Pat. No. 9,272,972, said application No. 15/494,985 is a continuation of application No. 14/307,232.

(51) Int. Cl.
*B01D 3/06* (2006.01)
*C07C 29/76* (2006.01)

(56) References Cited

FOREIGN PATENT DOCUMENTS

| | | |
|---|---|---|
| EP | 0848208 A2 | 6/1998 |
| WO | 2007073204 A1 | 6/2007 |
| WO | 2009017971 A1 | 2/2009 |
| WO | 20100080038 A1 | 7/2010 |
| WO | 2013074183 A1 | 5/2013 |

OTHER PUBLICATIONS

International Search Report and Written Opinion issued in the PCT Application PCT/US2015/034364, dated Aug. 25 2015 (12 pages).
International Preliminary Report on Patentability issued in the PCT Application PCT/US2015/034364, dated Dec. 20, 2016 (7 pages).
International Search Report and Written Opinion issued in the PCT Application PCT/US2014/021297, dated Jun. 25, 2014 (10 pages).

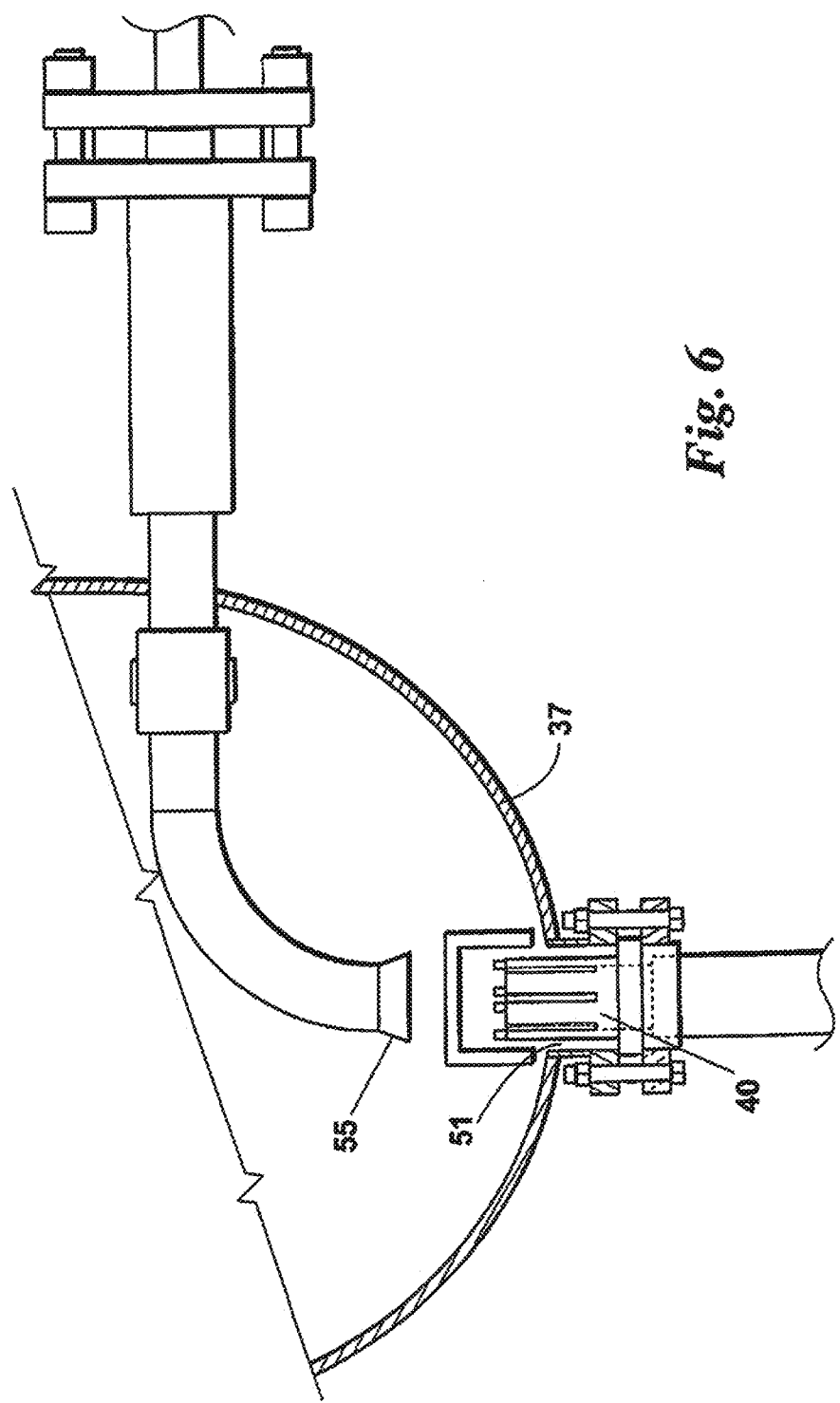

SALT REMOVAL AND TRANSPORT SYSTEM AND METHOD FOR USE IN A MONO ETHYLENE GLYCOL RECLAMATION PROCESS

CROSS-REFERENCE To RELATED APPLICATIONS

This application is a divisional application of U.S. patent application Ser. No. 15/494,985, filed Apr. 24, 2017 (U.S. Pat. No. 10,252,182), which is a continuation application that claims priority to U.S. patent application Ser. No. 15/056,256 filed Feb. 29, 2016 (U.S. Pat. No. 9,630,122), which claims priority to U.S. patent application Ser. No. 14/307,232 filed on Jun. 17, 2014 (U.S. Pat. No. 9,272,972), each of which is incorporated herein by reference. U.S. patent application Ser. No. 15/494,985 is also a continuation of U.S. patent application Ser. No. 14/307,232.

BACKGROUND

The present disclosure relates to processes designed to treat mono ethylene glycol (MEG) used in the oil and gas industry, especially in offshore locations, to control hydrates formation. More particularly, the present disclosure relates to MEG reclamation processes which are designed to remove salts and other contaminants from a wet MEG feed stream.

In the oil and gas industry, dry (lean) MEG is used to control the formation of hydrates within the produced stream. The now wet (rich) MEG is, in turn, dried by way of a MEG reclamation process so the MEG can be used again in hydrate control.

The unit used to recover MEG includes three sections: pre-treatment, flash separation, and MEG regeneration. Those sections can be followed by salt management and calcium removal sections.

In the pre-treatment stage, the rich MEG containing some dissolved gas and hydrocarbon liquids must pass through a three-phase separator vessel. The gas is flashed and recovered hydrocarbon liquids are sent to the production separator. The rich MEG is sent to a flash separator. The rich MEG stream comprised of produced water and MEG is fed to the flash separator where it is brought into contact with a hot recycle stream of MEG. The flash separator operates under vacuum. The MEG and water components of the rich MEG stream are flashed and exit through the top of the flash separator where they are sent to the MEG distillation column for regeneration. The salt components of the rich MEG stream precipitate in the flash separator.

The MEG regeneration section is a refluxed distillation column. The distillation column also operates under vacuum and distills the water from the MEG-water vapors coming off the top of the flash separator. Salt-free, lean MEG produced at the bottom of the distillation column is pumped to storage for reuse. The vaporized water passes overhead from the distillation column. The water is condensed and collected in the reflux drum. A small amount is returned to the distillation column as reflux, and the remaining is routed to treatment.

The salt crystals that precipitate in the flash separator are separated by gravity to the bottom of the brine column, where they are transferred to the salt tank. There, the salts are concentrated before removal through a centrifuge.

The salts in produced water cover a variety of species, but generally are categorized into monovalent salts (typically sodium and potassium), and divalent salts (typically calcium and magnesium). The divalent salts cannot be effectively precipitated in the same manner as the monovalent salts, so a separate calcium removal process may be installed. Effective calcium control is accomplished as the divalent salts are collected, reacted and removed through a centrifuge with the centrate overflow returning to the process.

Current methods of removing the salt crystals from bottom of the brine column involves a lot of equipment, including but not limited to complicated and expensive centrifugal filters or desanding cyclones, centrifuge pump filtration systems, a salt tank, a centrate tank, and a density measurement device. Reducing the footprint of the system used to remove the salt crystals is important for making more efficient use of space, reducing off-shore construction costs, and increasing ease of system operation and maintenance.

SUMMARY

In an embodiment, a system for removing solids from a process stream being fed into a flash separator includes a solids fluidization device and a solids removal device. The solids fluidization device is located at the bottom end of the fluid column of the flash separator and arranged to introduce a swirling motive fluid within the fluid column. The solids removal device is located above the solids fluidization device and arranged to remove the slurry created by the swirling motive fluid.

In an embodiment, a system for fluidizing solids in the fluid column of a flash separator includes a solids fluidization device that is located at the bottom end of the fluid column and arranged to introduce a swirling motive fluid within the fluid column and means to limit an upward movement of the swirling motive fluid within the fluid column. The means for limiting the upward movement may be a valve that is located above the solids fluidization device.

In an embodiment, a method of removing solids from a process stream being fed into a flash separator includes the isolation of a fluid in the fluid column of the flash separator from the upper end of the flash separator. A swirling motive fluid, which contacts the solid components of the isolated fluid, is introduced into the bottom end of the fluid column of the flash separator, and the solids slurry produced by the swirling motive fluid is removed.

In an embodiment, a method of fluidizing solids to aid in solids removal includes the introduction of a swirling motive fluid into the bottom end of the fluid column of the flash separator so that the swirling motive fluid contacts the solid components of a fluid in the fluid column. The method also includes limiting the upward movement of the swirling motive fluid within the fluid column and removing the solid slurry produced by the swirling motive fluid.

BRIEF DESCRIPTION OF THE DRAWINGS

So that the manner in which the above recited features can be understood in detail, a more particular description may be had by reference to embodiments, some of which are illustrated in the appended drawings, wherein like reference numerals denote like elements. It is to be noted, however, that the appended drawings illustrate various embodiments and are therefore not to be considered limiting of its scope, and may admit to other equally effective embodiments.

FIG. 6 is an enlarged view of the solids fluidization device of FIG. 1 and the removal device located directly above the solids fluidization device.

ELEMENTS AND NUMBERING USED IN THE DRAWINGS

Figure 1:
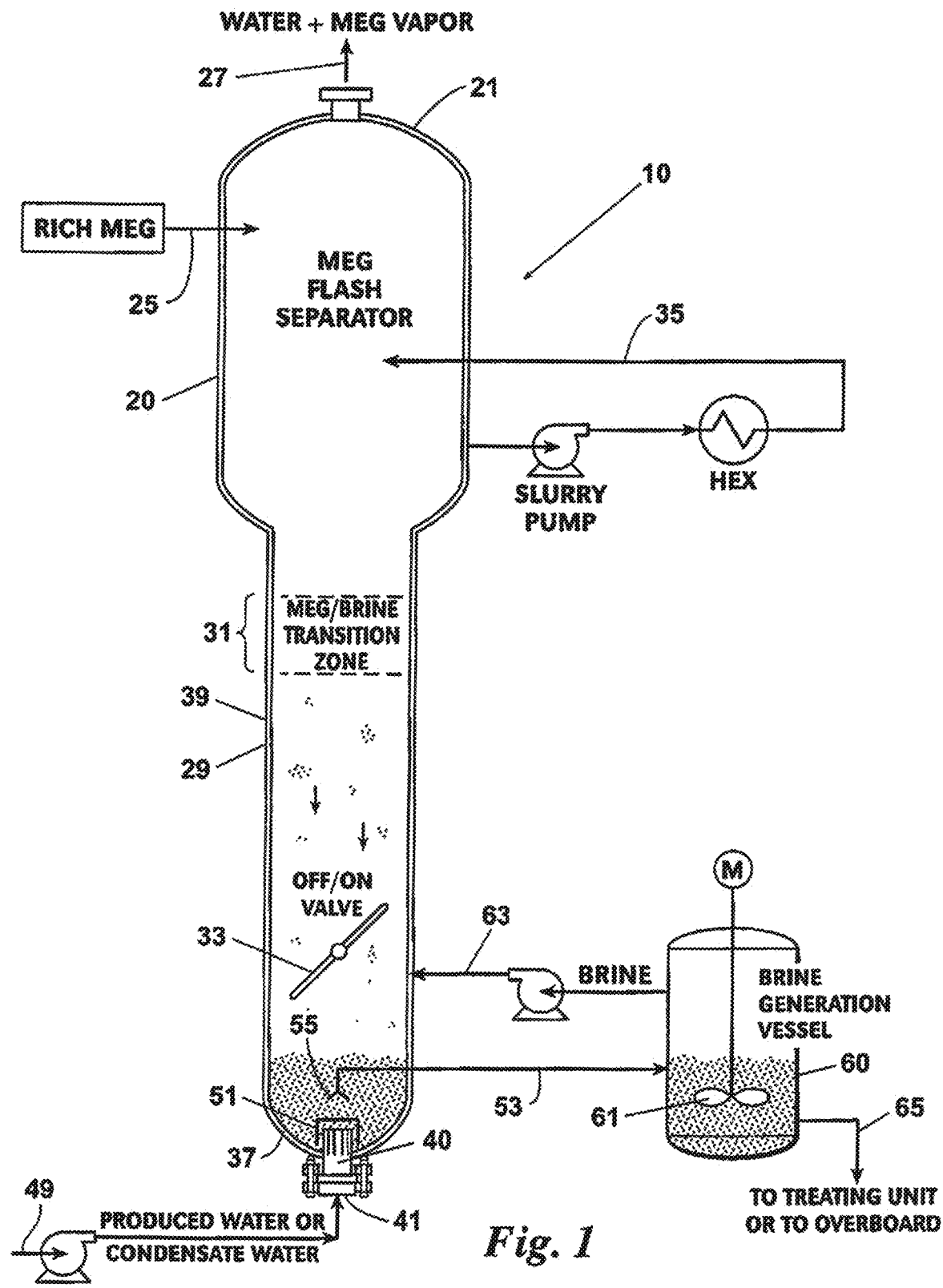
FIG. 1 is a schematic of an embodiment of a salt transport system for a MEG reclamation or recovery process. The system includes a solids fluidization device located at the bottom end of the brine column of a flash separator and an on-off valve located between the fluidization device and the MEG/brine transition zone of the flash separator.
Figure 3:
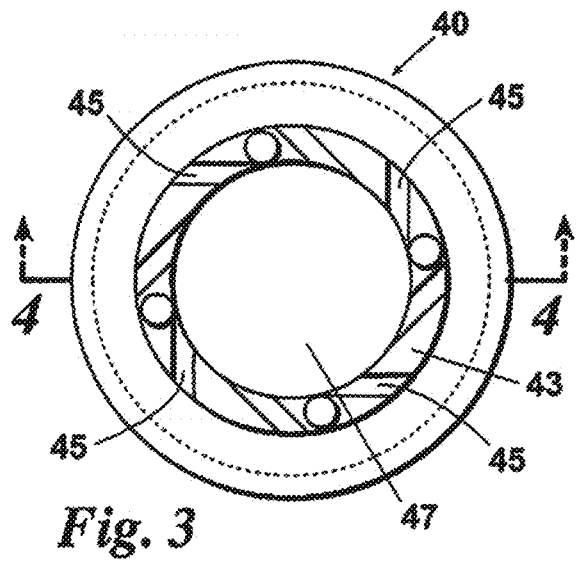
FIG. 3 is top view of the solids fluidization device of FIG. 2.
Figure 5:
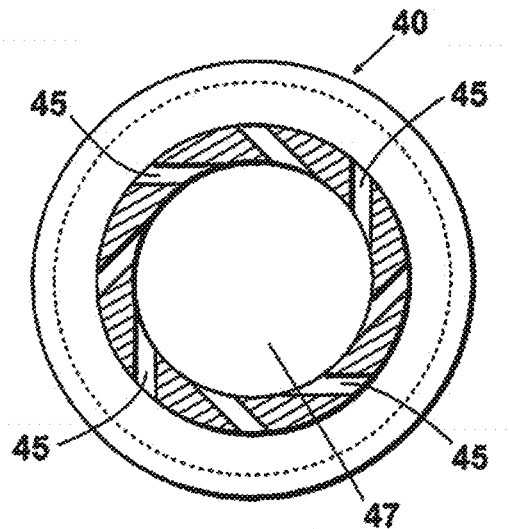
FIG. 5 is a cross-section view of the solids fluidization device of FIG. 2 taken along section line 5-5 of FIG. 2.
Figure 2:
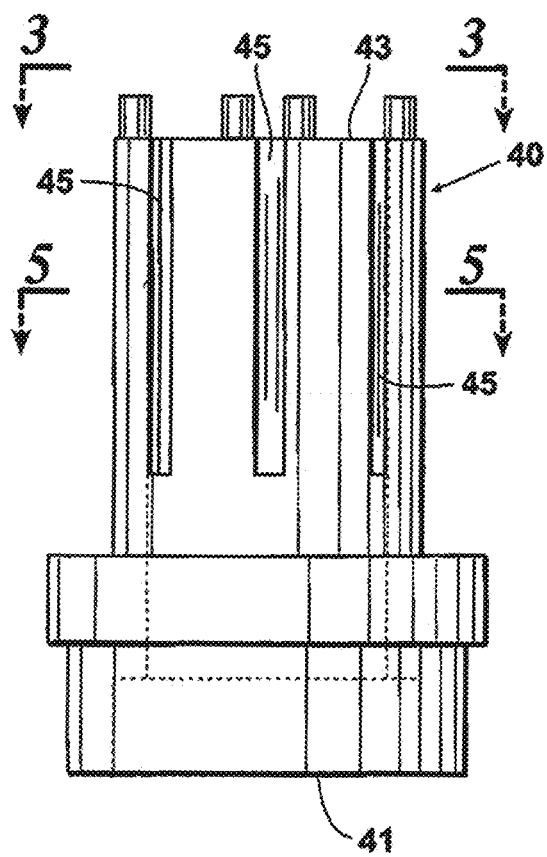
FIG. 2 is a front elevation view of the embodiment of the solids fluidization device of FIG. 1.
Figure 4:
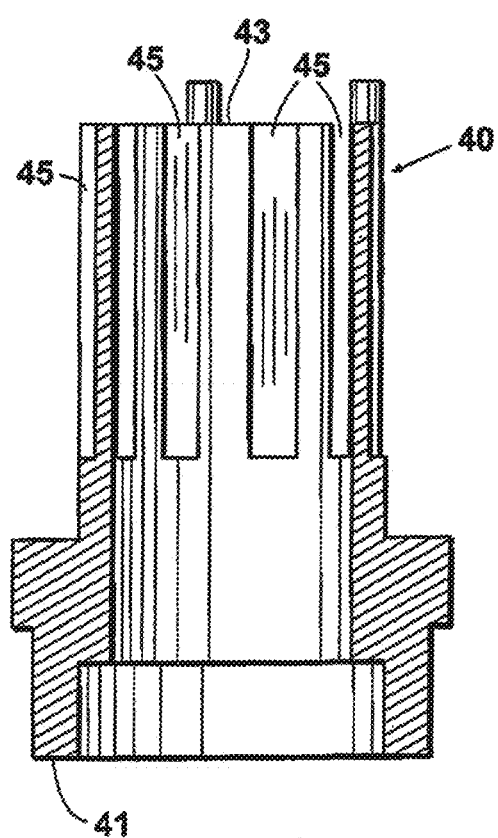
FIG. 4 is a cross-section view of the solids fluidization device of FIG. 2.

10 Salt transport system
20 Flash separator
21 Upper end
25 Rich (wet) MEG stream
27 Water and MEG vapor stream
29 Brine (fluid) or downcomer column or section
31 MEG/brine transition zone
33 On-off valve
35 Recycle loop
37 Bottom or lower end of 29
39 Upper end of 29
40 Sand removal device
41 Inlet
43 Upper end of 40
45 Slots
47 Inner bore
49 Produced or condensate (carrier or motive) water stream
51 Swirling motive fluid stream
53 Salt slurry stream
55 Removal device or slurry discharge head
60 Brine generation vessel
61 Agitator
63 Brine stream
65 Salt slurry (discharge) stream

DETAILED DESCRIPTION OF THE EMBODIMENTS

In the following description, numerous details are set forth to provide an understanding of some embodiments of the present disclosure. However, it will be understood by those of ordinary skill in the art that the system and/or methodology may be practiced without these details and that numerous variations or modifications from the described embodiments may be possible.

In the specification and appended claims, the terms "connect", "connection", "connected", "in connection with", and "connecting" are used to mean "in direct connection with" or "in connection with one or more elements"; and the term "set" is used to mean "one element" or "more than one element". Further, the terms "couple", "coupling", "coupled", "coupled together", and "coupled with" are used to mean "directly coupled together" or "coupled together via one or more elements". As used herein, the terms "up" and "down", "upper" and "lower", "upwardly" and "downwardly", "upstream" and "downstream", "above" and "below", and other like terms indicating relative positions above or below a given point or element are used in this description to more clearly describe some embodiments of the disclosure.

Referring first to FIGS. 1 and 6, an embodiment of a salt transport system 10 for a MEG recovery or reclamation process includes a flash separator 20 having a solids fluidization device 40 located at the bottom end 37 of the brine or downcomer column 29 and an on-off valve 33 located between the device 40 and the MEG/brine transition zone 31.

The flash separator 20 is of a kind well known in the art. In the separator 20 a rich (wet) MEG inlet stream 25 is brought into contact with a hot MEG recycle stream 35. The MEG and water components of the rich MEG stream 25 are flashed and exit the upper end 21 of the separator 20 as a water and MEG vapor stream 27. The salt components of the rich MEG inlet stream 25 precipitate in the brine (fluid) column 29 of the separator 20. A MEG/brine transition zone 31 forms in the column 29 between the MEG and the brine.

Solids fluidization device 40 is arranged at the bottom end 37 of the column 29. The device 40 includes means which produce or cause a swirling (e.g., vertiginous, rotary or cyclonic) motion or flow 51 of the motive fluid as it exits device 40. One suitable device 40 is a HYDROTRANS™ solids fluidization and removal device (Cameron Process Systems, Houston, Tex.). Any other device may be used as the fluidization device provided the device creates a swirling (e.g., vertiginous, rotating, or cyclonic) motive fluid flow when the flow exits the device.

Referring to FIGS. 2-5, the HYDROTRANS™ device includes a plurality of spaced-apart slots 45 arranged tangential to, surrounding, and in communication with an inner bore 47 which receives a motive fluid stream 49 at the lower inlet end 41 of the device. Motive fluid steam 49—which can be a produced water or condensate water stream (or some combination thereof)—exits the slots 45 of device 40 as a swirling motive fluid stream 51. The swirling motion of the motive fluid stream 51 mixes with the fluid containing solid/salt already residing in the column 29 to fluidize the salt components, thereby creating a salt slurry stream 53. By way of example, during the first five minutes of operation, the concentration of salt in the device 40 can be about 20 vol % on average.

Unlike a desanding hydrocyclone—which produce a cyclonic flow within the device but a straight over- and underflow exiting the device (i.e., straight in, cyclonic within, and straight out)—the solids fluidization device 40 produces this type of flow external to the device (i.e., straight in and rotary or cyclonic out).

The removal device 55, which can be a slurry discharge head, resides just above the upper end 43 of solids fluidization device 40. Removal device 55 carries the salt slurry stream 53 to a brine generation tank or vessel 60.

Because the brine in the column 29 is saturated with salt, adding produced water to it causes the lower density (not saturated) produced water 49 to flow to the upper end 39 of the column 29 and MEG to flow to the bottom end 37. This causes MEG loss. To prevent this loss from occurring, system 10 limits upward movement of the fluid, which can be by way of isolation means such as on-off valve 33, which may be a butterfly-type valve. When the valve 33 is in the off or closed position, it prevents the produced water from flowing to the upper end 39 of the column 29. The valve 33 isolates the fluid or brine located above and below the valve 33 from one another.

Once the salts are removed from the bottom end 37 of the column 29, the saturated brine in the brine generation vessel 60 is pumped back to the column 29 below the on-off valve 33 to replace the produced water. Once the produced water is replaced with the saturated brine, the on-off valve 33 is put in the on or open position to allow the salt to settle below the valve 33 and into the bottom 37 of column 29.

If a 1" HYDROTRANS™ is used as device 40, a flow rate of about 4 m$^3$/hr may be used to remove the salt from the bottom end 37. For about the first five minutes of operation, about 0.33 m$^3$ of a salt slurry stream 53 (about 20 vol %) is transferred to the brine generation vessel 60. Assuming a void space of 40% between the salt particles (i.e., the salt represents 60%), the total amount of salt removed in five minutes (0.083 hr) is 0.04 m$^3$ (4 m$^3$/hr×0.083 hr×0.2×0.6). The salt density is 2,165 kg/m$^3$. Therefore, the amount of salt removed in five minutes of operation (i.e., with the valve 33 closed) is about 87 kg. If the amount of salt settled at the bottom end 37 is higher (or lower) than in the example, the removal process can be adjusted accordingly.

In some embodiments, system 10 does not use any centrifugal filters or desanding cyclones to remove salt from the brine column 29, nor does it use centrifugal filtration, salt and centrate tanks, and density measurement devices. In other embodiments, system 10 uses less foot print than the prior art systems and methods, has lower construction costs, and is easier to operate and maintain.

After the salt removal process is completed, an agitator 61 can be used to agitate and dissolve the salt in the liquid phase within the brine generation vessel 60. The saturated brine solution can then be pumped as a saturated brine stream 63 to the column 29 to replace the produced water. Once this operation is complete, the valve 33 can be put in the on or open position to accumulate salt in the bottom end 37 of the column 29.

When the brine generation vessel 60 is filled with enough salt, agitator 60 will again be turned on to make a salt slurry stream 65 which is pumped to a water treating unit (not shown) or to overboard (if allowed).

In embodiments of a method of removing salt from a rich MEG stream which makes use of system 10 includes:
  i. isolating fluid in the brine column 29 of the flash separator 20 by closing a valve 33 located above the bottom end 37 of the brine column 29 and below the upper end 39 of the column 29;
  ii. introducing a swirling motive fluid stream 51 into the bottom end 37 of the brine column 29, the swirling motive fluid stream 51 coming into contact with salt components residing in the column 29 and forming a salt slurry stream 53;
  iii. removing the salt slurry stream 53 from the brine column 29 to a brine generation vessel 60;
  iv. agitating the contents of the brine generation vessel 60 to form a saturated brine 63;
  v. transferring the saturated brine 63 back to the column 29; and
  vi. opening the valve 33 after the transfer of the saturated brine 63 to the column 29 is complete.

Salt removal system 10 and the method for its use is an improvement over prior art systems and methods. The prior art makes use of complicated and expensive centrifugal filters or desanding cyclones to remove salt from the brine column 29 of the flash separator 20 along with centrifuge filtration, a salt tank, a centrate tank, and density measurement devices.

Embodiments of the system and method may (1) eliminate complicated and expensive centrifugal filters and desanding hydrocyclones to remove salt; (2) eliminate centrifuge filtration, a salt tank, a centrate tank, and density measurement devices; and (3) use less foot print than the prior art systems and methods and have lower construction costs and be easier to operate and maintain than those prior art systems and methods.

Although the preceding description has been described herein with reference to particular means, materials, and embodiments, it is not intended to be limited to the particulars disclosed herein; rather, it extends to all functionally equivalent structures, methods, and uses, such as are within the scope of the appended claims.

What is claimed:

1. A system for removing solids from a process stream being fed into a flash separator, the system comprising:
    a solids fluidization device located at a bottom end of a fluid column of the flash separator and arranged to introduce a swirling motive fluid within the fluid column; and
    a solids removal device located above the solids fluidization device and arranged to remove a slurry created by the swirling motive fluid.

2. The system of claim 1, further comprising means for limiting an upward movement of the swirling motive fluid in the fluid column.

3. The system of claim 2, wherein the means for limiting the upward movement of the swirling motive fluid in the fluid column is a valve located between a top end and a bottom end of the fluid column.

4. The system of claim 1, wherein the solids fluidization device includes a plurality of spaced-apart vertical slots arranged tangential to, surrounding, and in communication with a central inner bore of the solids fluidization device.

5. The system of claim 1, further comprising a brine generation vessel arranged to receive the slurry from the fluid column.

6. The system of claim 5, further comprising means for transporting a saturated brine from the brine generation vessel into the fluid column.

7. The system of claim 1, wherein a source of the swirling motive fluid is at least one of a produced water stream and a condensate water stream.

8. A system for fluidizing solids in a fluid column of a flash separator, the system comprising:
    a solids fluidization device located at a bottom end of the fluid column, wherein the solids fluidization device is arranged to introduce a swirling motive fluid within the fluid column; and
    means to limit an upward movement of the swirling motive fluid within the fluid column.

9. The system of claim 8, wherein the solids fluidization device includes a plurality of spaced-apart vertical slots arranged tangential to, surrounding, and in communication with a central inner bore of the solids fluidization device.

10. The system of claim 8, wherein the means for limiting the upward movement of the swirling motive fluid within the fluid column is a valve located above the solids fluidization device in the fluid column.

11. The system of claim 10, wherein the valve is a butterfly valve.

12. A system for removing solids from a process stream being fed into a flash separator, the system comprising:
    a solids rotary fluidization device located at a bottom end of a flash separator;
    a motive fluid source coupled to the solids rotary fluidization device outside the flash separator; and
    a solids removal device located above the solids fluidization device and arranged to remove a slurry created by the swirling motive fluid.

13. The system of claim 12, further comprising means for limiting an upward movement of the motive fluid in the flash separator.

14. The system of claim 13, wherein the means for limiting the upward movement of the motive fluid is a valve located between a top end and a bottom end of the flash separator.

15. The system of claim 12, further comprising a brine generation vessel arranged to receive the slurry from the flash separator.

16. The system of claim 15, further comprising a saturated brine conduit connecting the brine generation vessel to the flash separator.

17. The system of claim 16, wherein the saturated brine conduit is connected to the flash separator between a means for limiting an upward movement of the motive fluid and the solids rotary fluidization device.

18. The system of claim 17, wherein the saturated brine conduit is connected to the flash separator between the means for limiting an upward movement of the motive fluid and the solids removal device.

19. The system of claim 18, wherein the brine generation vessel comprises an agitator.

20. The system of claim 12, further comprising a divider between the solids rotary fluidization device and the solids removal device.

* * * * *